United States Patent [19]

Röeschlau et al.

[11] 4,164,448

[45] Aug. 14, 1979

[54] ACTIVATION OF CHOLESTEROL OXIDASE FOR CHOLESTEROL ASSAY

[75] Inventors: Peter Röeschlau; Gunter Lang; Klaus Beaucamp, all of Tutzing; Erich Bernt, Munich; Wolfgang Gruber, Tutzing-Unterzeismering Am Oberanger, all of Fed. Rep. of Germany

[73] Assignee: Boehringer Mannheim GmbH, Mannheim-Waldhof, Fed. Rep. of Germany

[21] Appl. No.: 768,530

[22] Filed: Feb. 14, 1977

Related U.S. Application Data

[63] Continuation of Ser. No. 529,669, Dec. 4, 1974, abandoned.

[30] Foreign Application Priority Data

Dec. 7, 1973 [DE] Fed. Rep. of Germany ....... 2361169
Aug. 16, 1974 [DE] Fed. Rep. of Germany ....... 2439348

[51] Int. Cl.$^2$ .................... C07G 7/02; G01N 31/14
[52] U.S. Cl. .................................................. 435/11
[58] Field of Search ................. 195/99, 101, 103.5 R, 195/62, 66 R, 63, 68, 127

[56] References Cited

U.S. PATENT DOCUMENTS

| 3,907,642 | 9/1975 | Richmond | 195/103.5 R |
| 3,992,158 | 11/1976 | Przybylowicz et al. | 195/103.5 R |

FOREIGN PATENT DOCUMENTS

2224132 11/1973 Fed. Rep. of Germany .... 195/103.5 R

*Primary Examiner*—David M. Naff
*Attorney, Agent, or Firm*—Sprung, Felfe, Horn, Lynch & Kramer

[57] ABSTRACT

Cholesterol oxidase free of unstabilizing residual traces of detergent is activated by adding to the cholesterol oxidase, before use thereof, at least one surface-active compound with lipophilic and hydrophilic properties. Diagnostic agents for determining cholesterol comprising cholesterol oxidase, a hydrogen peroxide detection system, a buffer, and at least one surface-active compound having lipophilic and hydrophilic properties are provided.

23 Claims, No Drawings

ACTIVATION OF CHOLESTEROL OXIDASE FOR CHOLESTEROL ASSAY

This is a continuation of application Ser. No. 529,669, filed Dec. 4, 1974, now abandoned.

The present invention relates to a process for the activation of cholesterol oxidase and to a diagnostic agent for determining cholesterol.

German Patent Specification No. 2,224,132 describes a process for the determination of cholesterol in which cholesterol is incubated in an aqueous medium with cholesterol oxidase, followed by the determination either of the oxygen consumption or of the amount of hydrogen peroxide or of cholestenone formed. This German Patent Specification also describes a reagent for the determination of cholesterol which comprises cholesterol oxidase and a system for the determination of hydrogen peroxide or a system for the determination of cholestenone.

We have now found that cholesterol oxidase has an insufficient storage stability and is inactivated relatively quickly. In the course of the investigation of this instability, we have found that the inactivation is brought about by small amounts of detergent which are present as an accompanying substance and originate from the process used for the preparation of the enzyme. This preparation of the enzyme can be carried out, for example, by the process described in German Patent Specification No. 2,224,131 in which a micro-organism which metabolizes cholesterol is digested by destruction of the cell walls with a non-ionic, surface-active agent present in a buffer solution and then extracted, whereafter the extract is centrifuged, the precipitate obtained is discarded and the supernatant liquid is applied to an anion exchanger, the enzyme then being eluted with a buffer solution containing the non-ionic surface-active agent and thereafter isolated from the eluate.

We have also found that, upon removal of these residual traces of detergent, a completely satisfactory storage stability of the enzyme can be achieved. However, we have also ascertained that the enzyme freed from detergent has a remarkably reduced activity. If, for example, the enzyme is used for the determination of cholesterol, then it is necessary either to use a comparatively freshly prepared preparation or considerably larger amounts of enzyme must be employed for the test or the time required for carrying out the determination must be considerably increased.

Consequently, there has been a need to provide a process for the activation of cholesterol oxidase.

The present invention provides such a process which, on the one hand, permits the use of cholestrol oxidase which is completely free from traces of detergent and, therefore, is sufficiently storage-stable and, on the other hand, provides an activity of the enzyme during use thereof which corresponds to that of the freshly prepared enzyme but which has not been subjected to the removal of small amounts of detergents.

The present invention provides a process for the activation of cholesterol oxidase, comprising adding at least one surface-active compound with lipophilic and hydrophilic properties to the cholesterol oxidase before the use thereof.

As surface-active compounds with lipophilic and hydrophilic properties, there are preferably used non-ionic detergents which contain at least one hydroxyl group in the molecule. Polyoxyethylene derivatives of alkyl, aryl and aralkyl alcohols are preferably employed. Examples of such preferred surface-active compounds include polyoxyethylene alkyl ethers, polyoxyethylene alkyl-carboxylic acid esters, polyoxyethylene-sorbitan alkyl carboxylic acid esters, polyoxyethylene-glycerol alkyl carboxylic acid esters, polyoxyethylene-alkylamines, polyoxyethylene-polyoxypropylene block polymers, polyoxyethylene-alkyl thioethers and polyoxyethylene alkyl aryl ethers. Specific examples thereof include hydroxy-polyethoxydodecane, ethyleneoxy adducts of alkylphenols, polyethoxy-ethylene derivatives of sorbitol anhydrides and the like. Polyoxyethylene derivatives modified with mercaptans are also equally suitable.

According to the present invention, the above-mentioned surface-active compounds are preferably used in an amount of between about 0.005 and 0.1 wt.%, referred to the aqueous enzyme solution.

Considerable numbers of the above-mentioned surface-active materials are commercially available and differ from one another by the number of oxyethylene groups present therein. The most useful ones are those which are water-soluble and which contain, on average, 5 to 20 oxyethylene groups per molecule. Lower oxyethylated types of compounds are usually only dispersible and are, therefore, less useful. Higher ethoxylated compounds (greater than 25) are admittedly water-soluble but are so hydrophilic that their effectiveness is reduced.

Similarly good results are also obtained with physiological surface-active substances which satisfy the above-given definition, for example, desoxycholates.

In addition, other surface-active substances with lipophilic and hydrophilic properties which contain at least one hydroxyl group, can also be used. Examples of such compounds include ethanol, butyl-diglycol and hex-yleneglycol. However, lower mono - and dialcohols of this type must be added in relatively large amounts of 10 to 20 vol.% for the achievement of the desired activation and the suitability thereof must be ascertained experimentally in each case. Thus, for example, no activation is achieved with methanol, ethylene glycol, polyethylene glycol, cyclohexanol, glycerol, lecithin and saponin. Surface-active compounds which have lipophilic and hydrophilic properties but which do not contain a hydroxyl group in the molecule can also be used.

Of the anionic wetting agents, the salts of bile acids, such as cholic acid, taurocholic acid and desoxycholic acid, are especially preferred, as well as fatty acid salts and fatty acid sarcosides. Of special importance are the sulfuric acid derivatives which, as is known, have the additional property of stabilizing the colored radical oxidation products of some indicators, such as o-tolidine and heterocyclic azines. These include, for example, the following classes of compounds: sulfosuccinic acid esters, alkyl aryl sulfonates, alkyl sulfates and alkyl polyoxyethylene sulfates.

Of the cationic wetting agents, there can be used, for example, alkyl pyridinium and trimethyl ammonium salts, as well as more complex compounds, for example, benzethonium chloride.

Of the amphoteric wetting agents, there can be used, for example, the imidazolium betaines.

Particular examples of surface-active compounds which can be used according to the present invention include sodium di(2-ethylhexyl)-sulfosuccinate, sodium dodecyl sulfate, sodium oleate, benzalkonium chloride and cetyl-pyridinium chloride.

The ionic or amphoteric detergents are preferably used in admixture with the above-mentioned non-ionic detergents, the appropriate amounts thereof corresponding to those of the non-ionic detergent.

The non-ionic, surface-active detergents containing at least one hydroxyl group in the molecule are preferred because they provide an approximately 5 to 10 times greater activation and thus a corresponding increase of the reaction velocity or shortening of the period of reaction in comparison with the other surface-active substances which can be employed. They are also effective in smaller amounts.

By alkyl groups, there are here to be understood those containing up to about 20 carbon atoms and especially those containing 12 to 18 carbon atoms.

The inactivation of cholesterol oxidase in the presence of traces of detergent is especially marked when the enzyme is present in ammonium sulfate solution. The following Table I shows the storage stability of the enzyme in 1 M ammonium sulfate solution at 33° C. in the presence of differing amounts of detergent. The experiments were carried out with an octyl-phenol-ethylene oxide adduct.

TABLE I

| storage period in days | Activity of cholesterol oxidase in %, referred to freshly prepared enzyme | | | |
|---|---|---|---|---|
| | | detergent | | |
| | without | 0.02% | 0.05% | 0.6% |
| 10 | 98% | 60% | 7% | 7% | 3% |
| 22 | 85% | 40% | 1% | 1% | 1% |

The effective amount of surface-active compound used in the process according to the present invention depends upon its molecular weight and upon the degree of its hydrophobic and hydrophilic properties. Too small an amount does not bring about an activation but too large an amount leads to the result generally known for surface-active substances of denaturing the enzyme. The appropriate concentration range, as well as the optimum concentration, can be experimentally determined for all appropriate surface-active agents. Such ranges are, for example, 0.15 to 0.6 wt.% for hydroxypolyethoxydodecane, 0.03 to 0.1 wt.% for octyl-phenol-ethylene oxide adducts, 0.15 to 0.6 wt.% for polyoxyethylene derivatives of sorbitol anhydrides, 0.03 to 0.05 wt.% for sodium desoxycholate and 0.005 to 0.02 wt.% for mercaptan-modified alkyl-phenol ethylene oxide adducts (for example Sterox SE).

Of the non-ionic surface-active polyoxy-ethylene compounds, those are especially useful which have a balance ratio of hydrophobic residues to polyoxyethylene chain and are water-soluble. A measurement value for the ratio of hydrophobic residue and polyoxyethylene chain is the so-called HLB value (cf. W. C. Griffin, J. Soc. Cosmetic, Chem., 1, 311/1950 and 5, 249/1954).

Those surface-active materials with HLB values between about 10 and 17 are especially useful. These values are, however, only to be regarded as being optimum standard values since the effectiveness also depends upon the nature of the hydrophobic residue.

The present invention is also concerned with a diagnostic agent for the detection and determination of cholesterol and of cholesterol esters in body fluids which can be used for carrying out the above-described process.

The determination of cholesterol is of considerable importance in medical diagnosis.

In clinical chemistry, rapid tests are being used more and more for the detection of substances in body fluids. Although they frequently do not provide sufficiently accurate results, nevertheless, they do permit a quicker and cheaper indication for routine and large-scale investigations. The diagnostic agents employed for rapid tests are either absorbent carriers or water-stable films which contain all of the reagents needed for the reaction. When these diagnostic agents are brought into contact with the body fluids to be tested, then color reactions are obtained which can be evaluated either on the basis of comparative colors or with the use of simple reflection photometers.

Experiments for the production of agents for cholesterol rapid tests by impregnation of absorbent paper with cholesterol oxidase, peroxidase, an oxidation indicator and a buffer do not give satisfactory results because the test papers thus obtained do not react with cholesterol-containing serum of the usual concentration.

We have now found that useful test papers or test films are obtained, which react in graduated stages with cholesterol-containing serum when the carrier additionally contains at least one of the above-described surface-active agents.

Thus, according to the present invention, there is also provided a diagnostic agent for the detection and determination of cholesterol and of cholesterol esters in body fluids which comprises a carrier or a synthetic resin film which is impregnated with or has embedded therein cholesterol oxidase, a system for the detection of hydrogen peroxide, a buffer and at least one of the above-described surface-active agents. The surface-active agent is preferably present therein in a concentration of 2 to 30% and more preferably of 10 to 20%, referred to the solid reagents.

A preferred system for the detection of hydrogen peroxide comprises peroxidase and an oxidation indicator, optionally together with a swelling agent and/or a stabilizer.

For the detection of cholesterol in serum, test papers are outstandingly useful which have been obtained by the impregnation of absorbent papers with the necessary reagents. If, however, it is desired to detect cholesterol in whole blood, then the test papers are preferably rendered hydrophobic, for example, in the manner described in German Patent Specification No. 1,598,048 or are coated with a semi-permeable membrane of cellulose esters. However, for the detection of cholesterol in whole blood, it is especially preferred to use test films, such as are obtainable according to German Patent Specification No. 1,598,153, containing the necessary reagents.

For the preparation of such test films, the reagents, for example, cholesterol oxidase, peroxidase, buffer, indicator and optionally a swelling agent, are stirred, together with the surface-active materials to be used according to the present invention, into an aqueous dispersion of a film-forming polymer. This dispersion is then coated as a thin film and left to dry. When cholesterol-containing blood is dropped on to such a reagent-containing film and then wiped off after about one minute, colorations are also obtained, the color depth of which depends upon the amount of cholesterol present in the blood. These colorations are particularly suitable for a quantitative evaluation with simple remission photometers.

The diagnostic agent according to the present invention can be used for the detection and determination of free cholesterol. If, however, cholesterol esters are also present, then the cholesterol must first be liberated therefrom. This can be carried out in known manner, for example, by saponification with aqueous alkali. However, it is particularly advantageous to split the ester with cholesterol esterase, which is preferably isolated from micro-organisms, since it is then possible to work under very mild conditions.

The cholesterol esterase can be added to the body fluid, followed by incubation. This process can be carried out, for example, by drawing the body fluid into capillaries, the inner walls of which are coated, in a manner analogous to that described in German Patent Specification No. 2,240,672, with cholesterol esterase and optionally with adjuvant materials. After incubation in the capillaries, the body fluid is then applied to the test strips in the above-described manner. If free and esterified cholesterol were both present in the body fluid, then, of course, the sum of the two is detected. However, the cholesterol esterase can also be incorporated especially advantageously into the test strips to give diagnostic agents with which, in one step, the sum of the free and esterified cholesterol can be detected and determined.

Systems which can be used for the detection of the hydrogen peroxide formed by the oxidation of the cholesterol, for example peroxidase, buffer, oxidation indicator and optionally a swelling agent and the like, are known, for example, for the descriptions of rapid tests for glucose. Examples of components for this preferred system are given in the following:

Of the peroxidases, that form horseradish is especially preferred but lactoperoxidase and the like can also be employed.

As buffers, there can be used those which are conventional, for example, phosphate, citrate and borate buffers. The pH value which they give on the diagnostic agent should be between 4 and 9 and preferably between 5 and 8.

As oxidation indicators, there can be used various classes of compounds, namely, benzidene derivatives, for example o-tolidine and o-vanillin derivatives according to German Patent Specification No. 1,598,133, or heterocyclic azines according to German Patent Specification No. 1,648,840.

The formulations for the diagnostic agents and especially those for test films, can also contain a conventional swelling agent, such as sodium alginate, carboxymethyl-cellulose or the like, as well as a stabilizing agent for the enzyme, for example dithioerythritol.

Substrate materials for test films are synthetic resin dispersions of, for example, polyvinyl propionate or acetate. Into these are stirred all the necessary reagents, preferably in dissolved form, whereafter the mixture obtained is then coated into thin films and dried.

Test papers can be produced by dissolving the reagents in water or in a mixture of water and organic solvents with which filter papers are impregnated and then dried. However, the paper can first be impregnated with the water-soluble reagents and then impregnated with, for example, the indicators in organic solution.

The following Examples are given for the purpose of illustrating the present invention without limiting same.

EXAMPLE 1

0.05 ml. of serum were added to 10 ml. 0.5 M potassium phosphate buffer of pH 7.5 which contained 0.4% hydroxypolyethoxydodecane. The extinction ($E_1$) was read off at 240 nm in a suitable spectrophotometer and the reaction started with 0.02 ml. (0.1 U) of storage-stable cholesterol oxidase, freed from traces of detergent, in 1 M aqueous ammonium sulfate solution. After 3 minutes, the extinction ($E_2$) was read off. The concentration of the cholestenone formed and thus of the cholesterol was given by the difference between the first and second readings, having regard to the molar extinction coefficients for cholesterol at 240 nm. The measurement of a typical sample gave 62 mg.% free cholesterol and 167 mg.% total cholesterol (after saponification).

A comparative determination but without the addition of the surface-active agent required a reaction time of 15 minutes.

The separation of traces of detergent for the improvement of the storage stability of the enzyme was preferably carried out with the use of hydrophobic adsorption resins. Especially preferred for this purpose were, for example, the material which was commercially available as "Bio-Beads" from Biorad, as well as the products obtainable from Rohm & Haas under the designation XAD-resins.

EXAMPLE 2

0.05 ml. serum were added to 10 ml. 0.5 M potassium phosphate buffer of pH 7.5 which contained 0.02% hydroxy-polyethoxy-dodecane and 0.03% sodium desoxycholate. The extinction ($E_1$) was read off at 240 nm in a suitable spectrophotometer and the reaction was started with 0.02 ml. (=0.1 U) storage-stable cholesterol oxidase, freed from traces of detergent, in 1 M aqueous ammonium sulfate solution.

After 3 minutes, the extinction ($E_2$) was again read off. The concentration of the cholestenone formed and thus of the cholesterol was given from the difference between the first and second readings, having regard to the molar extinction coefficients for cholestenone at 240 nm ($E=15.5$ cm$^2/\mu$ mol).

The measurement of a typical sample gave 65 mg.% free cholesterol and 170 mg.% total cholesterol (after saponification).

EXAMPLE 3

0.05 ml. serum were added to 10 ml. 0.5 M potassium phosphate buffer of pH 7.5 which contained 0.02% hydroxy-polyethoxydodecane and 0.1% secondary alkyl sulfate. The extinction ($E_1$) was measured at 240 nm in a suitable spectrophotometer and the reaction was started with 0.02 ml. (=0.1 U) storage-stable cholesterol oxidase, freed from traces of detergent, in 1 M aqueous ammonium sulfate solution.

After 3 minutes, the extinction ($E_2$) was again read off. The concentration of the cholestenone formed and thus of the cholesterol was given by the difference between the first and second readings, having regard to the molar extinction coefficients of cholestenone at 240 nm.

The measurement of a typical sample gave 62 mg.% free cholesterol and 167 mg.% total cholesterol (after saponification).

EXAMPLE 4

Filter paper (Schleicher & Schüll No. 597 NF Ind.) was impregnated with a solution of the following composition and dried at 40° C.:
1 M citrate buffer, ph 5.25—20 ml.
cholesterol oxidase (60 U/mg.)—0.1 g.
peroxidase (70 U/mg.)—0.05 g.
distilled water—ad 100 ml.

This paper was then impregnated with solutions of 0.2 g. o-tolidine in 100 ml. methylene chloride which, in addition, each contained 1 g. of the following surface-active materials:
(a) polyoxyethylene tributyl-phenol ether
(b) polyoxyethylene sorbitan monolaurate
(c) polyoxyethylene-nonyl-phenol ether
(d) polyoxyethylene lauryl ether
(e) polyoxyethylene cetyl ether
(f) polyoxyethylene stearate
(g) polyoxyethylene dodecyl thioether.

After drying, test papers were obtained which reacted with cholesterol-containing sera with a green color. If the sera also contained cholesterol esters, then stronger green colorations were obtained if the sera had previously been mixed with a drop of cholesterol esterase solution. A test paper which did not contain one of the above-mentioned surface-active materials did not react with the sera.

EXAMPLE 5

Filter paper (Schleicher & Schüll No. 597 NF Ind.) was impregnated with a solution of the following composition and dried at 40° C.:
1 M citrate buffer, pH 7—20 ml.
cholesterol oxidase (60 U/mg.)—0.1 g.
cholesterol esterase (18 U/mg.)—0.25 g.
peroxidase (70 U/mg.)—0.05 g.
distilled water—100 ml.

This paper was impregnated with solutions of 0.2 g. o-tolidine in 100 ml. methylene chloride which, in addition, each contained 0.5 g. of one of the following surface-active materials:
(a) polyoxyethylene cocoate
(b) polyoxyethylene oleate
(c) polyoxyethylene polypropylene glycol
(d) polyoxyethylene stearylamine
(e) polyoxyethylene glycerol monolaurate.

After drying, test papers were obtained which reacted with a green color with those sera which contained cholesterol and/or cholesterol esters. Test paper without surface-active agent showed no reaction.

Practically the same behavior was shown by test papers which contained the same amount of citrate buffer with a ph of 5.25 or 6.

EXAMPLE 6

Paper pre-impregnated in the manner described in Example 4 was subsequently impregnated with solutions of 0.3 g. o-tolidine in 100 ml. acetone which contained 1.5 g. of one of the following surface-active materials:
(a) dioctyl sodium sulfosuccinate
(b) sodium dodecyl-benzene-sulfonate
(c) sodium lauryl polyglycol ether sulfate
(d) sodium lauryl sarcosinate
(e) sodium laurate
(f) cholic acid
(g) desoxychloric acid
(h) sodium taurocholate These test papers possessed practically the same properties as the test papers produced according to Example 4 but the reaction colors were stable for a longer period of time.

Test papers with a phosphate buffer of pH possessed similar properties.

EXAMPLE 7

Paper pre-impregnated in the manner described in Example 5 was impregnated with solutions which contained 0.4 g. o-tolidine and 0.5 g. of one of the following surface-active materials:
(a) lauryl pyridinium chloride
(b) benzethonium chloride
(c) cetyl trimethyl ammonium chloride
(d) 1-hydroxyethyl-1-carboxymethyl-2-alkyl-imidazolinium betaine.

The properties of these test papers corresponded to those of Example 5.

EXAMPLE 8

Filter paper (Schleicher & Schüll No. 597 NF Ind.) was impregnated with a solution of the following composition and dried at 40° C.:
1 M phosphate buffer, pH 6—25 ml.
cholesterol oxidase (60 U/mg.)—0.1 g.
peroxidase (70 U/mg.)—0.05 g.
cholic acid—1.0 g.
acetone—10 ml.
distilled water—ad 100 ml.

This paper was subsequently impregnated with solutions of oxidation indicators in 100 ml. acetone.

The amount of indicator used, the chemical name thereof and the color reaction with cholesterol-containing sera were summarized in the following Table II:

TABLE II

| amount | indicator | colour reaction |
| --- | --- | --- |
| 0.3 g. | o-vanillylidene-n-vanilloyl-hydrazone | violet |
| 0.2 g. | azino-bis-(N-ethyl-benzthiazolone-2-sulphonic acid-5) diammonium salt | green |
| 0.1 g. | azino-bis-(N-alkylquinolone-2-sulphonic acid-6) di-ammonium salt | blue-violet |
| 0.1 g. | bis-(N-alkyl-quinolone-2)-azine | violet |
| 0.1 g. | (N-methyl-bensthiazolone-2)-N-ethyl-quinolone-2)-azine | blue-green |
| 0.3 g. | (N-methyl-benzthiazolone-2)-1-phenyl-3,4-dimethyl-triazolone-5)-azine | blue |

EXAMPLE 9

A mixture was prepared from the following components:
polyvinyl propionate dispersion—45 g.
sodium alginate, 1.85% in 0.5 M—35 g.
phosphate buffer, pH 5.5
cholesterol oxidase (60 U/mg.)—0.5 g.
peroxidase (70 U/mg.)—0.25 g.
dioctyl sodium sulfonsuccinate—1 g.
o-tolidine, dissolved in 6 ml. acetone—0.6 g.
water—50 ml.

This mixture was either spread out to give a film with a wet film thickness of about 300 nm or was painted on to a solid carrier and dried at 35° C. When blood containing cholesterol was dropped on to the film and the blood wiped off after one minute, then, depending upon the cholesterol concentration, green colorations of varying intensity were obtained.

If, in addition, 1.0 g. cholesterol esterase was added to the above-described formulation, then films were obtained with which it was also possible to determine increased cholesterol ester contents.

It will be understood that the foregoing specification and examples are illustrative but not limitative of the present invention inasmuch as other embodiments within the spirit and scope of the invention will suggest themselves to those skilled in the art.

What is claimed is:

1. Process for the activation of analytically pure, detergent-free, storage-stable cholesterol oxidase, recovered from a micro-organism by extraction with a surfactant, for the analytic determination of cholesterol which process comprises removing all traces of said surfactant from said cholesterol oxidase to produce a surfactant-free cholesterol oxidase and then adding to an aqueous solution of the surfactant-free cholesterol oxidase between 0.005% to 0.1% by weight, based on the weight of the aqueous cholesterol oxidase solution, of at least one surface-active compound with lipophilic and hydrophilic properties before use of said cholesterol oxidase.

2. Process as claimed in claim 1, wherein the surface-active compound used in non-ionic and contains at least one hydroxyl group.

3. Process as claimed in claim 2, wherein the non-ionic compound is a polyoxyethylene derivative of an aliphatic or aromatic alcohol.

4. Process as claimed in claim 1, wherein said surface-active compound is a polyoxyethylene derivative of alkyl, aryl and aralkyl alcohols.

5. Process as claimed in claim 4, wherein said derivative is a polyoxyethylene alkyl ether.

6. Process as claimed in claim 4, wherein said derivative is a polyoxyethylene alkyl carboxylic acid ester.

7. Process as claimed in claim 4, wherein said derivative is a polyoxyethylene-sorbitan alkyl carboxylic acid ester.

8. Process as claimed in claim 4, wherein said derivative is a polyoxyethylene-glycerol alkyl carboxylic acid ester.

9. Process as claimed in claim 4, wherein said derivative is a polyoxyethylene-alkylamine.

10. Process as claimed in claim 4, wherein said derivative is a polyoxyethylene-polyoxypropylene block polymer.

11. Process as claimed in claim 4, wherein said derivative is a polyoxyethylene-alkyl thioether.

12. Process as claimed in claim 4, wherein said derivative is a polyoxyethylene alkyl aryl ether.

13. Process as claimed in claim 1, wherein said surface-active compound is hydroxy-polyethoxydodecane.

14. Process as claimed in claim 1, wherein said surface-active compound is an ethyleneoxy adduct of alkyl-phenols.

15. Process as claimed in claim 1, wherein said surface-active compound is a polyethoxy-ethylene derivative of sorbitol anhydrides.

16. Process as claimed in claim 1 wherein said surface-active compound is used in an amount of from 0.005% to 0.6% by weight.

17. Diagnostic agent in solid form for the detection and determination of cholesterol and cholesterol esters in body fluids which comprises a solid carrier having impregnated or embedded therein cholesterol oxidase, a system for the detection of hydrogen peroxide, buffer and from 2 to 30%, based on the total solid diagnostic agent of at least one surface-active compound with lipophilic and hydrophilic properties.

18. Diagnostic agent as claimed in claim 17, wherein the carrier is impregnated with said surface-active compound.

19. Diagnostic agent as claimed in claim 17, wherein the surface-active agent is present therein in a concentration of 10 to 20%, referred to the solid reagents.

20. Diagnostic agent as claimed in claim 17, wherein cholesterol esterase is also present.

21. Diagnostic agent as claimed in claim 17 wherein at least one of a swelling and stabilizing agent is also present.

22. Diagnostic agent as claimed in claim 17 wherein said carrier is an absorbent carrier impregnated with cholesteroloxidase.

23. Diagnostic agent as claimed in claim 17 wherein said carrier is a synthetic resin film having embedded therein cholesteroloxidase.

* * * * *